United States Patent
Park et al.

(10) Patent No.: US 9,745,606 B2
(45) Date of Patent: Aug. 29, 2017

(54) MICROALGAE AURANTIOCHYTRIUM SP. LA3 (KCTC12685BP) AND METHOD FOR PREPARING BIO-OIL USING THE SAME

(71) Applicant: SK Innovation Co., Ltd., Seoul (KR)

(72) Inventors: Joong Min Park, Seoul (KR); Chang Kuk Kim, Seoul (KR); Yeon Hwa La, Daejeon (KR); Young Bin Seo, Seoul (KR)

(73) Assignee: SK Innovation Co., Ltd., Seoul (KR)

( * ) Notice: Subject to any disclaimer, the term of this patent is extended or adjusted under 35 U.S.C. 154(b) by 26 days.

(21) Appl. No.: 14/813,689

(22) Filed: Jul. 30, 2015

(65) Prior Publication Data
US 2016/0102328 A1  Apr. 14, 2016

(30) Foreign Application Priority Data

Oct. 8, 2014  (KR) .................. 10-2014-0135586

(51) Int. Cl.
| | |
|---|---|
| *C12P 7/64* | (2006.01) |
| *C12N 1/12* | (2006.01) |
| *C11B 1/02* | (2006.01) |
| *C11B 1/04* | (2006.01) |
| *C11B 1/10* | (2006.01) |
| *C11B 3/00* | (2006.01) |
| *C11B 3/10* | (2006.01) |
| *C11B 3/14* | (2006.01) |
| *C11B 7/00* | (2006.01) |
| *C12R 1/89* | (2006.01) |

(52) U.S. Cl.
CPC ............ *C12P 7/6409* (2013.01); *C11B 1/025* (2013.01); *C11B 1/04* (2013.01); *C11B 1/10* (2013.01); *C11B 3/001* (2013.01); *C11B 3/008* (2013.01); *C11B 3/10* (2013.01); *C11B 3/14* (2013.01); *C11B 7/0075* (2013.01); *C12N 1/12* (2013.01); *C12R 1/89* (2013.01)

(58) Field of Classification Search
CPC ..... C12P 7/6427; C12P 7/6472; C12P 7/6463; C12P 23/00; C12P 7/64; C12P 7/6409; C12P 7/649; C12P 5/007; A61K 31/202; A61K 2300/00; A61K 8/361; A61K 31/201; A61K 35/68; A61K 31/20; A61K 31/232; A61K 2035/11; C12N 1/12; C11B 1/025; C11B 1/04; C11B 1/10; C11B 3/00; C11B 3/001; C11B 3/008; C11B 3/10; C11B 3/14; C11B 7/0075; C12R 1/89

See application file for complete search history.

(56) References Cited

U.S. PATENT DOCUMENTS

| | | |
|---|---|---|
| 5,130,242 A | 7/1992 | Barclay |
| 5,340,742 A | 8/1994 | Barclay |
| 6,582,941 B1 | 6/2003 | Yokochi et al. |

FOREIGN PATENT DOCUMENTS

JP    1997000284 A    1/1997

OTHER PUBLICATIONS

Ellenbogen, B.B. et al., "Polyunsaturated Fatty Acids of Aquatic Fungi: Possible Phylogenetic Significance", Comp. Biochem. Physiol., 1969, pp. 805-811, vol. 29, Pergamon Press, Great Britain.

*Primary Examiner* — Debbie K Ware
(74) *Attorney, Agent, or Firm* — The Webb Law Firm

(57) ABSTRACT

Provided herein are microalgae of a Thraustochytrid and a method for preparing bio-oil using the same, and more particularly, *Aurantiochytrium* sp. LA3 (KCTC12685BP) having bio-oil producibility, and a method of preparing bio-oil, particularly bio-oil having a content of omega-3 unsaturated fatty acids of 30% by weight or more based on total fatty acids, characterized by culturing the microalgae. The microalgae *Aurantiochytrium* sp. LA3 (KCTC12685BP) described herein has a rapid sugar consumption rate when being cultured using glucose as a carbon source, has a high oil content, allows cells to be cultured at a high concentration, and allows oil to be obtained in high productivity and a high yield, and thus, may produce bio-oil more economically and environmentally friendly.

9 Claims, 1 Drawing Sheet

```
                          SEQUENCE LISTING

<160> NUMBER OF SEQ ID NOS: 3

<210> SEQ ID NO 1
<211> LENGTH: 996
<212> TYPE: DNA
<213> ORGANISM: Aurantiochytrium sp. LA3

<400> SEQUENCE: 1
agattaagcc atgcatgtgt aagtataagc gattgtactg tgagactgcg aacggctcat      60
tatatcagta ataatttctt cggtagtttc ttttatatgg atacctgcag taattctgga     120
aataatacat gctgtaagag ccctgtatgg ggctgcactt attagattga agccgatttt     180
attggtgaat catgataatt gagcagattg acttttttag tcgatgaatc gtttgagttt     240
ctgccccatc agttgtcgac ggtagtgtat tggactacgg tgactataac gggtgacgga     300
aagttagggc tcgactccgg aaagggagcc tgaaagacgg ctaccatatc caaggatagc     360
atcaggcgcg taaattaccc actggggact ccacgaggta gtgacgagaa atatcgatgc     420
gaagcgtgta tgcgttttgc tatcggaatg aaagcaatgt aaaaccctca tcgaggatca     480
actggagggc aagtctgggg ccagcagccg cggtaattcc agctcccaaa tgaatgctaa     540
agttgttgca gttaaaaagc tcgtagttga atttctggca agggcgaccg gtgctttccc     600
tgaatgggga ttgattgtct gtgttgcctt ggccctcttt tgcttctctt ttcggggaga     660
aatctttcac ggtaatcaaa gcaaagggtt caagcaggtc gtatgaccgg tatgttatta     720
tgggatgaaa aataggactt gggtgtattt tgtgggttgc cgcctgagaa gggtaatagg     780
aaagttgggg gtatcgtatt aggagctaga gtgaattctg gattccgaag acgactagag     840
cgaggcatta ccagcaggtt tcattatcaa gacgaaggcg gggatcgaga tgatagatac     900
atcgagtcta accgtaacga tgcgactgcg atgttggggc ttttatgggc tcaccgcagc     960
catggaaacc aagctttggg tccgggggga ttggtc                               996

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
aacctggttg atcctgccag                                                  20

<210> SEQ ID NO 3
<211> LENGTH: 24
<212> TYPE: DNA
<213> ORGANISM: Artificial Sequence
<220> FEATURE:
<223> OTHER INFORMATION: Primer

<400> SEQUENCE: 3
ttgttacgac gacttcacct tcct                                             24
```

MICROALGAE AURANTIOCHYTRIUM SP. LA3 (KCTC12685BP) AND METHOD FOR PREPARING BIO-OIL USING THE SAME

CROSS-REFERENCE TO RELATED APPLICATION

This application claims priority to Korean Patent Application No. 10-2014-0135586 filed Oct. 8, 2014, the disclosure of which is hereby incorporated in its entirety by reference.

The Sequence Listing associated with this application is filed in electronic format via EFS-Web and is hereby incorporated by reference into the specification in its entirety. The name of the text file containing the Sequence Listing is 155686_ST25.txt. The size of the text file is 2,076 bytes, and the text file was created on Jul. 28, 2015.

TECHNICAL FIELD

The present invention relates to microalgae of a Thraustochytrid and a method for preparing bio-oil using the same, and more particularly, to *Aurantiochytrium* sp. LA3 (KCTC12685BP) having bio-oil producibility, and a method of preparing bio-oil, particularly bio-oil having a content of an omega-3 unsaturated fatty acid of 30 wt % or more based on total fatty acids, characterized by culturing the microalgae.

BACKGROUND ART

Unsaturated fatty acids are also called, highly unsaturated fatty acids or poly unsaturated fatty acids (PAUF). Particularly the unsaturated fatty acids useful to a human body are an omega-3 (ω-3) fatty acid and an omega-6 (ω-6) fatty acid, and the omega-3 fatty acid has a double bond at the third carbon, and the omega-6 fatty acid does not have a double bond before the sixth carbon. Representative examples of the omega-3 unsaturated fatty acid include docosahexaenoic acid (DHA) having a carbon chain length of 22 with 6 double bonds starting from the third carbon from the methyl end, and represented by "22:6n-3", eicosapentaenoic acid (EPA) represented by "20:5n-3", docosapentaenoic acid (DPA) represented by "22:5n-3", α-linolenic acid represented by "16:3n-3", and the like, which are known as very useful kinds of an omega-3 unsaturated fatty acid, and the omega-6 unsaturated fatty acid includes arachidonic acid (ARA) represented by "20:4n-6", and the like.

The unsaturated fatty acids as the above play a very important role in a body: it is known that the omega-3 unsaturated fatty acid prevents arteriosclerosis and a coronary heart disease, mitigates an inflammatory condition, and delays growth of tumor cells; and the omega-6 unsaturated fatty acid functions as a structural lipid in a human body, and also as a precursor of numerous factors in inflammation such as prostaglandin, leukotriene and oxylipin. Particularly, docosahexaenoic acid (DHA) is known as an essential fatty acid in brain, an ocular tissue, and a nervous system, particularly having an important function in development of eyesight and psychomotor ability of an infant, and abundant in retina, semen and a brain tissue of a human being and an animal. Particularly, DHA is an essential fatty acid constituting 60% of brain fat. The docosahexaenoic acid is known as being important for healthy development of brain, eyes, and a nervous system of an infant, together with arachidonic acid (ARA), and has been reported to be effective in prevention and treatment of numerous diseases ranging from cancer to arthritis, cardiovascular diseases, and mental disorders, and recently, its various anti-aging functions such as suppression of macular degeneration of presbyopia have been newly discovered.

Since such omega-3 or omega-6 unsaturated fatty acid has an important function in a human body, it is recommended by the World Health Organization (WHO) that omega-3 unsaturated fatty acid should account for 1-2% of daily energy intake, which corresponds to about 2.2 to 4.4 g based on 2000 kcal of meal, and it is recommended by certified organizations in each country to consistently take 1 g or more of DHA a day. Therefore, DHA has been commercialized as various products such as health functional food, and also has high potential as pharmaceutical raw materials, and thus, it can be said that the commercial value of DHA is very high.

However, since such omega-3 or omega-6 unsaturated fatty acid is not naturally synthesized in a human body, there is a difficulty that those fatty acids should be ingested mainly through food.

Previously, the omega-3 or omega-6 unsaturated fatty acid has been ingested through vegetable oil, marine animal oil, fish oil, oilseeds, and the like, and representatively has been supplied by direct ingestion of fish oil contained in fish. The fish containing a high content of EPA and DHA is mackerel, herring, salmon, and the like, and some fish such as cod and haddock reserves most of fat in liver. Nevertheless, the best source is cold water fish such as tuna, mackerel, sardines, herring and trout. However, in order to efficiently receive DHA from fish oil, it is preferred to eat raw or boiled fish, and moreover, it is necessary to eat peel in rear gill of dorsal circumference and along abdomen, because most of oil is accumulated in those parts. However, since fish oil decays rapidly, and decayed fish smells fishy odor, it has a disadvantage of not whetting appetite very much, and has a serious pollution problem by heavy metals and organic chemical materials of the fish oil. Particularly, in order to obtain fish oil in a sufficient amount to a human body, a large amount of fish is needed, and thus, practically, it is very difficult to meet such requirements economically on an industrial scale.

In order to solve these problems, research of a method of preparing omega-3 unsaturated fatty acid including docosahexaenoic acid by culturing various microorganisms including algae has proceeded. Particularly, interest in fine-heterotrophic bacteria called Thraustochytrid has been increased, which are a non-photosynthetic heterotrophic microorganism group classified into Stramenophila kingdom together with oomycetes and labyrinthulids. Thraustochytrid includes *Schizochytrium, Aurantiochytrium* and *Thraustochytrium* genera, and the species constituting those genera have been spotlighted as a potential omega-3 source for industrial use, due to their high lipid content and high level of DHA. Thraustochytrid is a saprobe, or in some cases, a trivial name of fine heterotrophic bacteria supplied as a saprophyte. Thraustochytrid has wide geographical distribution together with strain separated from the Antarctic Continent, the North Sea, India, Japan and Australia. It is rarely found in living plants, and appears to be inhibited by plant antimicrobials. The species constituting this group are abundant sometimes in a dead autochthonous organism of indigenousness macro-algae, aquatic Mangrove leaves and the like, as well as allochthonous plant materials. They are present usually in water column including coast and deep sea, and in a deposit.

A preparation method of omega-3 unsaturated fatty acid by *Thraustochytrium* and *Schizochytrium* genera microorganisms which are a kind of marine microalgae has been already known since the late 1960s (Ellenbogen B. B. et al., *Comp. Biochem. Physiol.*, 29:805-811, 1969), and Martek which is estimated to have the most advanced technology has developed a method of producing omega-3 unsaturated fatty acid using *Schizochytrium* sp. ATCC 20888 and *Schizochytrium* sp. ATCC 20889 which are microorganisms of a *Schizochytrium* genus (U.S. Pat. Nos. 5,130,242B and 5,340,742B). In addition, Suntory has reported *Schizochytrium limacinum* SR21 as a microorganism having excellent docosahexaenoic acid productivity (Japanese Patent Laid-Open Publication No. 1997-000284A, and U.S. Pat. No. 6,582,941B).

There are still a number of researches in progress, however, a demand for new microalgae having high productivity and process efficiency, and particularly an ability to environmentally friendly mass-produce bio-oil is urgent.

Accordingly, the present inventors exerted all efforts to develop microalgae having high unsaturated fatty acid producibility, while having high efficiency of a culture process, and as a result, confirmed that microalgae of a Thraustochytrid were separated from a coastal wetland or a hot springs area wetland having a high temperature and rich in organic materials, and in case of using the microalgae, omega-3 and additionally omega-6 unsaturated fatty acids may be efficiently and economically produced, and thus, completed the present invention.

SUMMARY OF THE INVENTION

An object of the present invention is to provide microalgae having high unsaturated fatty acid productivity, and improving efficiency of a culture process, thereby allowing bio-oil to be prepared economically.

Another object of the present invention is to provide a method of preparing bio-oil using the microalgae.

In order to achieve the above objects, the present invention provides microalgae, *Aurantiochytrium* sp. LA3 (KCTC 12685BP) having bio-oil producibility.

Further, the present invention provides a method of preparing bio-oil, the method comprising the steps of: (1) culturing the microalgae *Aurantiochytrium* sp. LA3 (KCTC 12685BP); and (2) extracting and separating bio-oil containing omega-3 unsaturated fatty acid from the cultured microalgae.

DETAILED DESCRIPTION OF THE INVENTION

Figure 1:
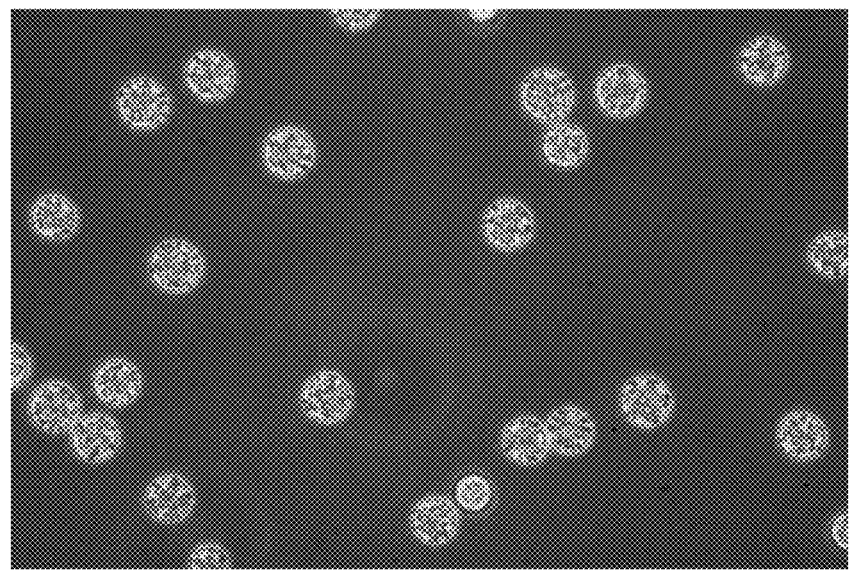
FIG. 1 is a microphotograph of the microalgae, *Aurantiochytrium* sp. LA3 (KCTC12685BP) of the present invention.

In the present invention, in order to develop microalgae having high unsaturated fatty acid producibility, microalgae of a Thraustochytrid has been separated from a coastal wetland or a hot springs area wetland having a high temperature and rich in organic materials.

Therefore, in one aspect, the present invention relates to microalgae *Aurantiochytrium* sp. LA3 (KCTC 12685BP) having bio-oil producibility.

The microalgae of the present invention, *Aurantiochytrium* sp. LA3 (KCTC12685BP) is the microalgae of a Thraustochytrid, and has omega-3 and omega-6 unsaturated fatty acid producibility.

The microalgae of the present invention is microalgae separated from floating matter in a coastal wetland or a hot springs area wetland, and may have a DNA sequence of a 18S rRNA gene indicated as SEQ ID NO: 1. As a result of search by NCBI (National Center for Biotechnology Information) Blast, it was found to be novel microalgae of a Thraustochytrium family, and deposited in a gene bank of Korean Collection for Type Cultures, Korea Research Institute of Bioscience and Biotechnology (KRIBB), 125 Gwahak-ro, Yuseong-gu, Daejeon 305-806, Republic of Korea as *Aurantiochytrium* sp. LA3, Accession No. KCTC12685BP on Sep. 26, 2014.

The bio-oil prepared by *Aurantiochytrium* sp. LA3 (KCTC12685BP) according to the present invention may have a content of an omega-3 unsaturated fatty acid of 30 wt % or more based on total fatty acids.

*Aurantiochytrium* sp. LA3 (KCTC12685BP) provided by the present invention has advantages of having a rapid sugar consumption rate when being cultured using glucose as a carbon source, having a high oil content, and allowing cells to be cultured at a high concentration, thereby obtaining oil in high productivity and a high yield.

In another aspect, the present invention provides a method of preparing bio-oil, the method comprising the step of: (1) culturing the microalgae *Aurantiochytrium* sp. LA3 (KCTC 12685BP); and (2) extracting and separating bio-oil containing omega-3 unsaturated fatty acid from the cultured microalgae.

In the present invention, culturing in above step (1) may be carried out in a manner selected from the group consisting of batchwise, fed-batchwise, and continuous culturing, and in above step (2), a cell disruption step may be further included.

The cell disruption may be cell disruption using a supersonic disperser, cell disruption using a pulsed electric field, cell disruption using an enzyme, cell disruption using osmotic pressure, cell disruption using an electron beam, or cell disruption using an organic solvent.

The method of preparing bio-oil of the present invention may further comprise (3) purifying bio-oil containing the omega-3 fatty acid.

In the present invention, the purification may include collecting only an oil phase among an oil phase containing bio-oil and an aqueous phase containing cell pieces, and may be carried out by including one or more steps of removing a solidified oil fraction, bleaching using bleaching clay or activated carbon, filtering, and deodorizing.

In the present invention, the deodorizing step may be carried out by a steam deodorizing process under reduced pressure.

In one embodiment of the present invention, the method of preparing bio-oil containing omega-3 fatty acid using the *Aurantiochytrium* sp. LA3 (KCTC12685BP) may comprise the following steps:

(1) culturing *Aurantiochytrium* sp. LA3 (KCTC12685BP); and (2) collecting the cultured *Aurantiochytrium* sp. LA3 (KCTC12685BP), and extracting and separating bio-oil containing omega-3 unsaturated fatty acid.

The method may further comprise:

(3) purifying bio-oil containing the separated omega-3 unsaturated fatty acid.

Hereinafter, each step will be described in detail.

Culturing of *Aurantiochytrium* sp. LA3 (KCTC12685BP) in above step (1) may proceed in a manner selected from batchwise, fed-batchwise and continuous culturing, and it is preferred to use fed-batchwise or continuous culturing.

In step (1), it is preferred to supply a carbon source for culturing *Aurantiochytrium* sp. LA3 (KCTC12685BP) through the fed-batchwise or continuous culturing. Herein, the carbon source may be used without limitation only if it grows using *Aurantiochytrium* sp. LA3 (KCTC12685BP), and glucose, fructose, sucrose, galactose, glycerol, crude glycerol which is biodiesel waste, and the like are preferred, but not limited thereto, and glucose is most preferred. It is preferred that the carbon source is supplied in a continuous or fed-batchwise manner so as to maintain proper concentration, and if necessary, a method such as pH-stat or DO-stat may be used, and a method of supplying the carbon source as required by measuring the concentration of each carbon source in real time, and the like may also be used. In addition, a nutrient needed for growth of *Aurantiochytrium* sp. LA3 (KCTC12685BP) may be contained in a medium, and it is apparent to a person skilled in the art that a variety of a nitrogen source, a phosphate source, other components, and the like may be contained, and also a complex medium, a defined medium, or the like may be used. As the nitrogen source, an organic nitrogen source such as yeast extract, corn steep liquor, beef extract, malt extract, peptone, tryptone, and the like, and an inorganic nitrogen source such as acetate, ammonium nitrate, ammonium sulfate, sodium nitrate, urea, and the like may be used.

Particularly, it is preferred to set salt concentration to an appropriate concentration level and proceed with culturing within the range.

In step (1), it is preferred to maintain pH and/or temperature within a predetermined range, during culturing *Aurantiochytrium* sp. LA3 (KCTC12685BP) through fed-batchwise or continuous culturing. As the way to constantly maintain pH and/or temperature during culturing, a well-known method in the art, such as a method of using a cooling jacket with cooling water, a method of using a pH controller to automatically supply acid or base, and the like, may be used, but not limited thereto.

Further, it is preferred that culturing of *Aurantiochytrium* sp. LA3 (KCTC12685BP) through the fed-batchwise or continuous culturing, is carried out under adequate aeration and agitation. An aeration speed and an agitation speed may be appropriately selected by a person skilled in the art according to a process condition. More specifically, since *Aurantiochytrium* sp. LA3 (KCTC12685BP) is aerotropic, and has a property of being weak under shear stress by agitation, it is preferred that agitation speed may be selected from 50-300 rpm, preferably 100-300 rpm, and aeration speed may be 0.5-5 vvm, preferably 1-3 vvm.

The content of an omega-3 unsaturated fatty acid in the bio-oil produced through culturing of step (1) according to the present invention is 30 wt % or more, preferably 40 wt % or more, most preferably 50 wt % or more, based on total fatty acids.

The step to collect the cultured *Aurantiochytrium* sp. LA3 (KCTC12685BP), and extract and separate bio-oil containing an omega-3 unsaturated fatty acid according to step (2), includes a step to disrupt cells, after completing the culturing in step (1). In the step of cell disruption, cell disruption may be induced by methods of cell disruption using a pulsed electric field, cell disruption using an enzyme, cell disruption using an electron beam, and the like, but not limited thereto, and it is apparent to a person skilled in the art that a method of using an organic solvent such as hexane to disrupt cells and extract oil, may be used. Particularly, if the disruption technique is used after cell disruption using osmotic pressure, a cell disruption effect may be enhanced.

As the cell disruption proceeds, phase separation of an oil phase and an aqueous phase containing cell pieces occurs, and only the oil phase is collected at this time, and a final bio-oil product may be obtained through a purification process in step (3).

The purification of bio-oil according to step (3) is carried out by including one or more steps selected from the group consisting of leaving the oil phase at −5-0° C. for 5-20 hours to remove a solidified oil fraction, bleaching the oil fraction using bleaching clay and/or activated carbon, filtering, and deodorizing, and preferably, those steps may be sequentially carried out.

It is preferred to carry out filtering using a filter having a pore size of 0.5-1 μm, and it is also preferred to carry out deodorizing through a steam deodorization process under reduced pressure, but not limited thereto.

Hereinafter, the present invention will be described in detail through the following Examples. These Examples are only for specifically illustrating the present invention, and it is apparent to a person skilled in the art that according to the gist of the present invention, the scope of the present invention is not limited to these Examples.

Example 1. Separation of Microalgae

In order to screen microalgae having excellent bio-oil producibility, microalgae of a Thraustochytrid family were separated from floating matters in a coastal wetland or a hot springs area wetland, in the following manner.

A sample of floating matters was added to 50 mL of a medium containing 10 g/L of glucose, 2 g/L of yeast extract, 2 g/L of peptone, 1 g/L of $KH_2PO_4$, and 30 g/L of sea salt, and cultured for a day. 50 mL of the obtained culture fluid was smeared on a solid medium containing 10 g/L of glucose, 2 g/L of yeast extract, 2 g/L of peptone, 1 g/L of $KH_2PO_4$, 30 g/L of sea salt and 15 g/L of agar, and thereafter, cultured at 28° C. for 5 days to obtain seven colonies, and the obtained seven colonies were subcultured 4 times to be purely separated.

Each of the colonies was cultured in a 50 mL shaking incubator at 28° C. for 4 days at 150 rpm using 5 mL of a liquid medium (glucose 60 g/L, corn steep liquor 14.4 g/L, sea salt 10 g/L, potassium phosphate monobasic 1 g/L, glutamic acid 3 g/L, sodium sulfate 5 g/L, ammonium sulfate 1 g/L, calcium chloride 0.4 g/L, magnesium sulfate 2 g/L, ferric sulfate 1 mg/L, zinc sulfate 1 mg/L, manganese (II) chloride 3 mg/L, cobalt(II) chloride 0.04 mg/L, sodium molybdate 0.04 mg/L, copper(II) sulfate 2 mg/L, nickel(II) sulfate 2 mg/L, and thiamin 1 mg/L), cultured in a 250 mL shaking incubator at 28° C. for 3 days at 150 rpm using 50 mL of the liquid medium, cultured in a 1000 mL shaking incubator at 28° C. for a day at 150 rpm using 400 mL of the liquid medium, and thereafter, cultured in a 5 L jar fermentor at 28° C., 200 rpm, 0.7 vvm and initial pH 7.0 using 2 L of the liquid medium. Cultured microbial cells were collected, respectively, and subjected to disruption with a supersonic disruptor, and oil was extracted with 100 mL of hexane therefrom, and thereafter, the extracted oil was analyzed for fatty acid compositions in the oil with an AOCS (American Oil Chemists' Society) method.

Figure 2:
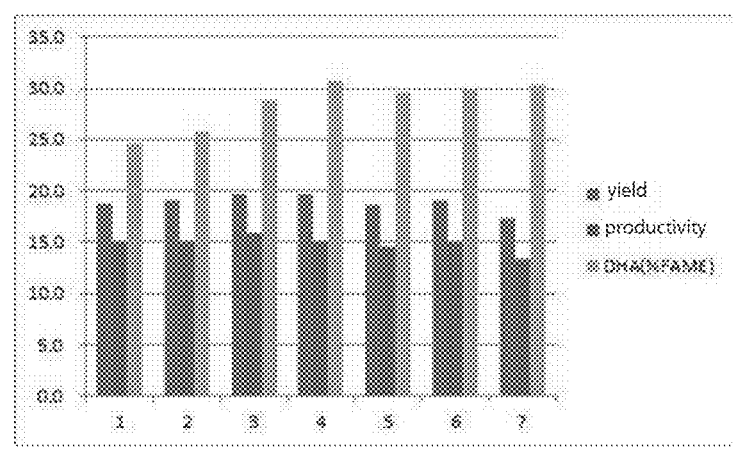
FIG. 2 is a graph representing bio-oil yields, productivities, and DHA fractions in total fatty acids with culturing time of seven microalgae colonies separated in the present invention.

Among the separated seven colonies, a microbial cell #4 having the highest oil producibility and yield, and containing 30 wt % or more of an omega-3 fatty acid in total fatty acids was screened (FIGS. 1 and 2).

Example 2. Identification Through 18S DNA Analysis

For molecular biological identification of the finally screened strain #4, a 18S rRNA gene sequence was analyzed. After chromosomal DNA was separated from one colony, 18S rRNA gene DNA was amplified by a PCR method, using primers for amplification of a 18S rRNA gene of microalgae of a Thraustochytrid family, F: 5'-AACCTG-GTTGATCCTGCCAG-3' (SEQ ID NO: 2) and R: 5'-TT-GTTACGACGACTTCACCTTCCT-3' (SEQ ID NO: 3). After removing a salt, an amplified reaction solution was analyzed by Macrogen Corporation for a base sequence, and the sequence was identified as SEQ ID NO: 1. As a result of search through NCBI (National Center for Biotechnology Information) Blast, the screened strain was found to be novel microalgae of a *Thraustochytrium*, and deposited in a gene bank of Korean Collection for Type Cultures as *Aurantiochytrium* sp. LA3 (KCTC12685BP) on Sep. 26, 2014.

Example 3. Analysis of Growth and Bio-Oil Production Characteristics of *Aurantiochytrium* sp. LA3 (KCTC12685BP) Under Batchwise Culture Condition Growth and bio-oil production characteristics of microalgae, *Aurantiochytrium* sp. LA3 (KCTC12685BP) separated from Example 1 were researched and analyzed under a batchwise culture condition.

Single *Aurantiochytrium* sp. LA3 (KCTC12685BP) colony cultured in a solid medium was selected, and cultured at 28° C. for 4 days at 150 rpm, using 5 mL of a liquid medium {(glucose g/L, yeast extract 4.8 g/L, potassium chloride 1 g/L, potassium phosphate monobasic 2 g/L, glutamic acid sodium salt 3 g/L, sodium sulfate 12 g/L, calcium chloride 0.5 g/L, magnesium sulfate 2 g/L, trace elements (ethylenediaminetetraacetic acid 18 mg/L, ferric sulfate 0.87 mg/L, boric acid 20.52 mg/L, zinc sulfate 0.711 mg/L, manganese(II) chloride 2.58 mg/L, cobalt(II) chloride 0.078 mg/L, sodium molybdate 0.015 mg/L, copper(II) sulfate 0.006 mg/L, nickel(II) sulfate 0.156 mg/L), and vitamins (thiamin 0.6 mg/L, biotin 0.0015, cobalamin 0.015 mg/L, calcium pantothenate 0.6 mg/L)}, cultured at 28° C. for 3 days at 150 rpm, using 50 mL of the liquid medium, cultured at 28° C. for a day at 150 rpm, using 400 mL of the liquid medium, and thereafter, batch-cultured in a 5 L fermentor at 28° C., 200 rpm, 0.7 vvm, and initial pH 7.0, using 2 L of a liquid medium (glucose 120 g/L, corn steep liquor 28.8 g/L, potassium chloride 1 g/L, potassium phosphate monobasic 2 g/L, glutamic acid sodium salt 3 g/L, sodium sulfate 12 g/L, calcium chloride 0.5 g/L, magnesium sulfate 2 g/L, trace elements, and vitamins). Cultured microbial cells were collected, respectively, and subjected to disruption with a supersonic disruptor, and oil was extracted with 100 mL of hexane therefrom, and thereafter, the extracted oil was analyzed for fatty acid compositions in the oil with an AOCS (American Oil Chemists' Society) method.

As a result, all glucose in the medium was consumed in 36 hours, and 49.7 g/L of microbial cells were obtained at this time (Table 1). As a result of extracting oil in microalgae from the obtained microbial cells, an oil content relative to a dry weight of microalgae was 51.2 wt %, and a DHA content relative to fatty acids was 33.6 wt %.

TABLE 1

| Cell density (g/L) | Oil content (%) | DHA (% FAME) | yield | productivity |
|---|---|---|---|---|
| 49.7 ± 5.4 | 51.2 ± 7.5 | 33.6 ± 2.9 | 20.7 ± 3.1 | 17.0 ± 3.0 |

Example 4. Analysis of Growth and Bio-Oil Production Characteristics of *Aurantiochytrium* sp. LA3 (KCTC12685BP) Under Fed-Batchwise Culture Condition Growth and bio-oil production characteristics of microalgae, *Aurantiochytrium* sp. LA3 (KCTC12685BP) separated from Example 1 were researched and analyzed under a fed-batchwise culture condition.

Single *Aurantiochytrium* sp. LA3 (KCTC12685BP) colony cultured in a solid medium was selected, and cultured at 28° C. for 4 days at 150 rpm, using 5 mL of a liquid medium {(glucose g/L, yeast extract 4.8 g/L, potassium chloride 1 g/L, potassium phosphate monobasic 2 g/L, glutamic acid sodium salt 3 g/L, sodium sulfate 12 g/L, calcium chloride 0.5 g/L, magnesium sulfate 2 g/L, trace elements (ethylenediaminetetraacetic acid 18 mg/L, ferric sulfate 0.87 mg/L, boric acid 20.52 mg/L, zinc sulfate 0.711 mg/L, manganese(II) chloride 2.58 mg/L, cobalt(II) chloride 0.078 mg/L, sodium molybdate 0.015 mg/L, copper(II) sulfate 0.006 mg/L, nickel(II) sulfate 0.156 mg/L), and vitamins (thiamin 0.6 mg/L, biotin 0.0015, cobalamin 0.015 mg/L, calcium pantothenate 0.6 mg/L)}, cultured at 28° C. for 3 days at 150 rpm, using 50 mL of the liquid medium, cultured at 28° C. for a day at 150 rpm, using 400 mL of the liquid medium, and thereafter, fed-batch-cultured in a 5 L fermentor at 28° C., 250 rpm, 0.7 vvm, and initial pH 7.0, using 1 L of a liquid medium (glucose 60 g/L, corn steep liquor 14.4 g/L, potassium chloride 1 g/L, potassium phosphate monobasic 2 g/L, glutamic acid sodium salt 3 g/L, sodium sulfate 12 g/L, calcium chloride 0.5 g/L, magnesium sulfate 2 g/L, trace elements, and vitamins). When a residual amount of sugar is 10-20 g/L, 420 g/L of glucose was fed twice by 0.5 L to finally obtain 2 L of a culture fluid. Cultured microbial cells were collected, respectively, and subjected to disruption with a supersonic disruptor, and oil was extracted with 100 mL of hexane therefrom, and thereafter, the extracted oil was analyzed for fatty acid compositions in the oil with an AOCS (American Oil Chemists' Society) method.

As a result, all glucose in the medium was consumed in 60 hours, and 109.9 g/L of microbial cells were obtained at this time (Table 2). As a result of extracting oil in microalgae from the obtained microbial cells, an oil content relative to a dry weight of microalgae was 60.2 wt %, and a DHA content relative to fatty acids was 30.7 wt %.

TABLE 2

| Cell density (g/L) | Oil content (%) | DHA (% FAME) | yield | productivity |
|---|---|---|---|---|
| 109.9 ± 3.0 | 60.2 ± 1.2 | 30.7 ± 1.3 | 24.2 ± 0.2 | 26.4 ± 0.2 |

The microalgae *Aurantiochytrium* sp. LA3 (KCTC12685BP) according to the present invention has a rapid sugar consumption rate when being cultured using glucose as a carbon source, has a high oil content, allows cells to be cultured at a high concentration, and allows oil to be obtained in high productivity and a high yield, and thus, may produce bio-oil more economically and environmentally friendly.

The present invention has been described in detail in specific parts, and it is obvious that such specific technique is only a preferred embodiment to a person skilled in the art, without limiting the scope of the present invention thereby. Thus, the substantial scope of the present invention will be defined by the appended claims and their equivalents.

The invention claimed is:

1. A method of preparing bio-oil, the method comprising the steps of:
   (1) culturing microalgae *Aurantiochytrium* sp. LA3 (KCTC 12685BP); and
   (2) extracting and separating bio-oil containing omega-3 unsaturated fatty acid from the cultured microalgae.

2. The method of claim 1, wherein the bio-oil comprises 30 wt % or more omega-3 unsaturated fatty acid based on total fatty acids.

3. The method of claim 1, wherein the culturing of step (1) is carried out in a manner selected from the group consisting of batchwise, fed-batchwise, and continuous culturing.

4. The method of claim 1, wherein step (2) further comprises a cell disruption step.

5. The method of claim 4, wherein the cell disruption is carried out in a manner selected from the group consisting of a supersonic disperser, a pulsed electric field, an enzyme, osmotic pressure, an electron beam, and an organic solvent.

6. The method of claim 1, further comprising the step of (3) purifying bio-oil containing the omega-3 fatty acid.

7. The method of claim 6, wherein the purification comprises collecting only an oil phase among an oil phase containing bio-oil and an aqueous phase containing cell pieces.

8. The method of claim 6, wherein the purification comprises one or more steps selected from the group consisting of removing a solidified oil fraction, bleaching using bleaching clay or activated carbon, filtering, and deodorizing.

9. The method of claim 8, wherein the deodorizing is carried out by a steam deodorizing process under reduced pressure.

* * * * *